US012558102B2

(12) United States Patent
Tamura et al.

(10) Patent No.: US 12,558,102 B2
(45) Date of Patent: Feb. 24, 2026

(54) TREATMENT DEVICE

(71) Applicant: OLYMPUS CORPORATION, Hachioji (JP)

(72) Inventors: Toshinori Tamura, Hachioji (JP); Toshihiro Yoshii, Hachioji (JP); Motoi Satake, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 560 days.

(21) Appl. No.: 17/965,343

(22) Filed: Oct. 13, 2022

(65) Prior Publication Data

US 2023/0034974 A1 Feb. 2, 2023

Related U.S. Application Data

(63) Continuation of application No. PCT/JP2020/016554, filed on Apr. 15, 2020.

(51) Int. Cl.
A61B 17/128 (2006.01)
A61B 17/122 (2006.01)
A61B 17/00 (2006.01)

(52) U.S. Cl.
CPC ........ A61B 17/1285 (2013.01); A61B 17/122 (2013.01); *A61B 2017/00367* (2013.01); *A61B 2017/00477* (2013.01)

(58) Field of Classification Search
CPC . A61B 17/122; A61B 17/1227; A61B 17/128; A61B 17/1285
See application file for complete search history.

(56) References Cited

U.S. PATENT DOCUMENTS

2006/0259049 A1* 11/2006 Harada ................ A61B 17/122
606/151
2019/0231353 A1* 8/2019 Saenz Villalobos ........................
A61B 17/1285

FOREIGN PATENT DOCUMENTS

JP       S50-038691 U      4/1975
JP       2003-000607 A     1/2003
JP       2005-013540 A     1/2005
(Continued)

OTHER PUBLICATIONS

Jul. 7, 2020 International Search Report issued in International Patent Application No. PCT/JP2020/016554.

*Primary Examiner* — Todd J Scherbel
(74) *Attorney, Agent, or Firm* — Oliff PLC

(57) ABSTRACT

A treatment device includes an indwelling device including a treatment portion, and a tubular member including a proximal-end opening and in which a proximal-end portion of the treatment portion is disposed. The treatment device further includes an actuator including a connector releasably connected to a proximal-end portion of the treatment portion, and a power transmission member connected to the connector for moving the connector. The treatment portion can be fixed with respect to the tubular member when the power transmission member is retracted such that connector pulls the proximal-end portion of the treatment portion in a proximal direction to a predetermined position. The treatment device also includes a regulation portion for regulating a displacement of the connector in a direction separating from a longitudinal axis of the tubular member in the state in which the connector pulls the proximal-end portion towards the predetermined position.

20 Claims, 11 Drawing Sheets

(56)         References Cited

FOREIGN PATENT DOCUMENTS

| JP | 5750620 | B2 | 7/2015 |
| JP | 2019-520902 | A | 7/2019 |
| WO | 2018/011847 | A1 | 1/2018 |
| WO | 2018/063984 | A1 | 4/2018 |

* cited by examiner

FIG. 16

TREATMENT DEVICE

This application is a continuation application of PCT International Application No. PCT/JP2020/016554, filed Apr. 15, 2020. The content of the PCT International Application is incorporated herein by reference.

TECHNICAL FIELD

The present disclosure relates to a treatment device, more specifically, relates to a treatment device for ligating tissues.

BACKGROUND

As a treatment performed by using an endoscope, a ligation using a treatment device having a treatment portion such as a clip unit or the like is known. The clip unit includes a pair of arms. When the pair of arms is pulled by a predetermined amount while the pair of arms are clamping the tissue, the pair of arms are locked with the tissue strongly clamped therebetween.

The clip unit is introduced into the body while being attached to an actuator. Since the clip unit is indwelled in the body with the tissue ligated, it is necessary to separate the clip unit from the actuator after the pair of arms are locked.

A known clip unit has a configuration in which a proximal-end portion of a pair of arms is accommodated in a pressing tube. The proximal-end portion of the arms is connected to the operation wire.

When the operation wire is pulled to pull the proximal-end portion of the arms out of the pressing tube by a predetermined amount for canceling a connection between the arms and the operation wire, the arms are locked in a closed state. Therefore, the arms tending to be closed can be opened by pushing the operation wire until the proximal end portion of the arms is pulled out of the pressing tube by a predetermined amount.

The structure of the known clip unit is configured to make the arm open again for re-grasping the tissue in a case in which the arms sandwich the tissue at an inappropriate position.

On the other hand, in order to cancel the connection between the arms and the operation wire, it is necessary to advance the operation wire, and two operations of pulling and pushing the operation wire are necessary to lock and indwell the arms.

SUMMARY

According to an aspect of the present disclosure, a treatment device includes an indwelling device including a treatment portion capable of being indwelled in a specimen, and a tubular member including a proximal-end opening, and in which a proximal-end portion of the treatment portion is accommodated. The treatment device also includes an actuator including a connector releasably connected to the proximal-end portion of the treatment portion, and a power transmission member connected to the connector for moving the connector. The connector may be arranged at a distal-end side of the proximal-end opening of the tubular member in a state in which the connector is connected to the proximal-end portion of the treatment portion and the treatment portion protrudes beyond the distal end of the tubular member. The treatment portion can be fixed with respect to the tubular member when the power transmission member is retracted such that the connector pulls the proximal-end portion of the treatment portion in a proximal direction to a predetermined position. The treatment device also includes a regulation portion for regulating a displacement of the connector in a direction separating from a longitudinal axis of the tubular member in the state in which the connector pulls the proximal-end portion of the treatment portion towards the predetermined position.

According to another aspect of the present disclosure, a clip device includes a pressing tube that extends from a distal end toward a proximal end and includes a proximal-end opening; arms that are openable and closable a connector releasably connected to the arms; and a regulation portion. At least part of the arms can be accommodated in the pressing tube, and the arms can include an engaging portion for fixing the arms to the pressing tube by engaging with the proximal-end opening. The connector may be arranged at a distal-end side of the proximal-end opening of the pressing tube in a state in which the arms protrude from the distal end of the pressing tube. The regulation portion can regulate a displacement of the connector in a direction separating from a longitudinal axis of the pressing tube in a state in which the engaging portion is engaged with the proximal-end opening.

BRIEF DESCRIPTION OF DRAWINGS

FIG. 16 is a partial cross-sectional view showing a processing during the usage of the ligation device.

DESCRIPTION OF EMBODIMENTS

An exemplary embodiment of the present disclosure will be described with reference to FIG. 1 to FIG. 12.

Figure 1:
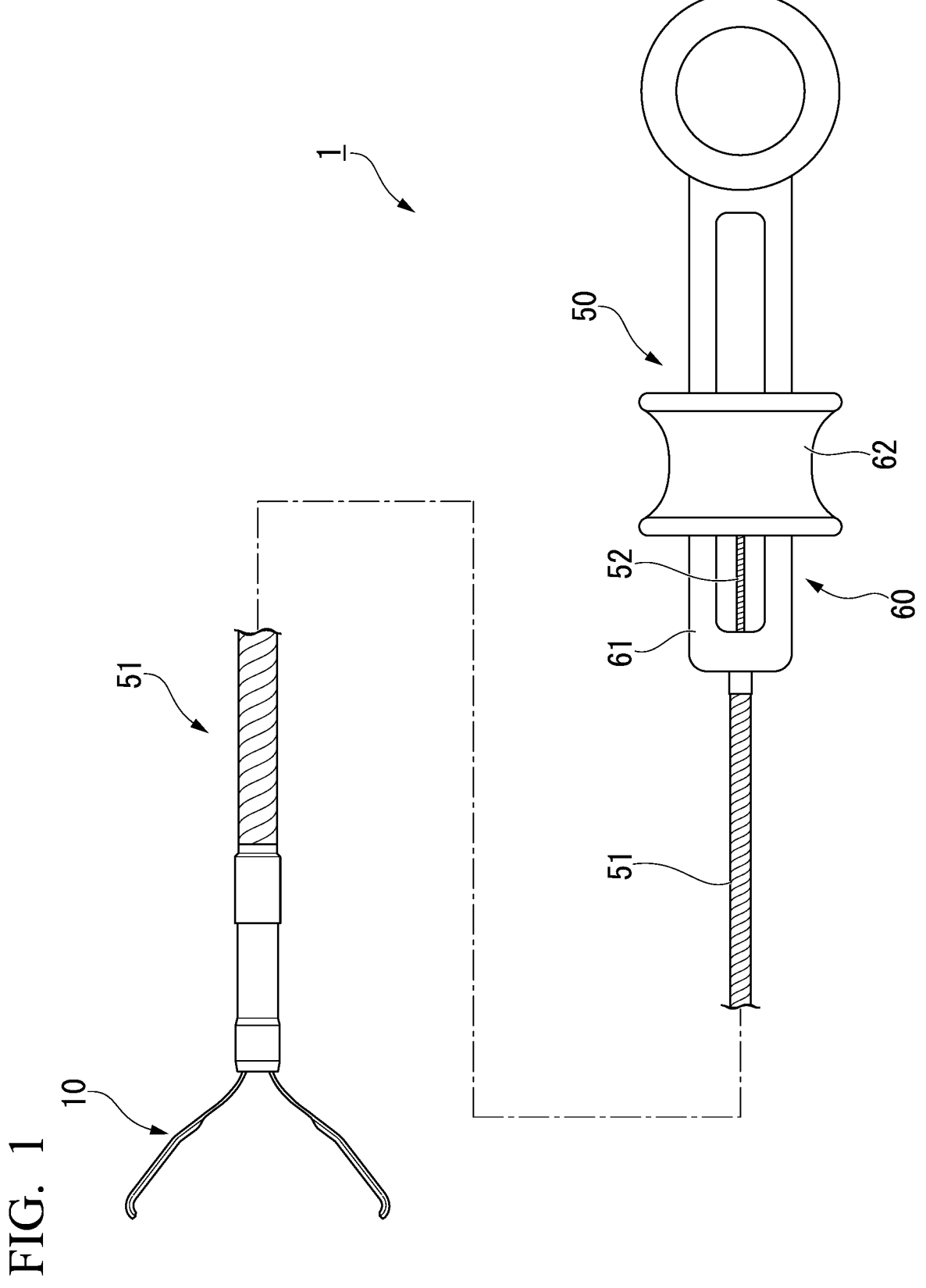
FIG. 1 is a view showing an overall configuration of a ligation device according to an exemplary embodiment of the present disclosure.

FIG. 1 is a view showing an appearance of a ligation device 1 as the treatment device according to the present embodiment. The ligation device 1 includes a clip unit (indwelling device) 10 that is indwelled in the body and an actuator 50 for operating the clip unit 10. The clip unit 10 is attached to a tip end (distal end) of the actuator 50.

Figure 2:
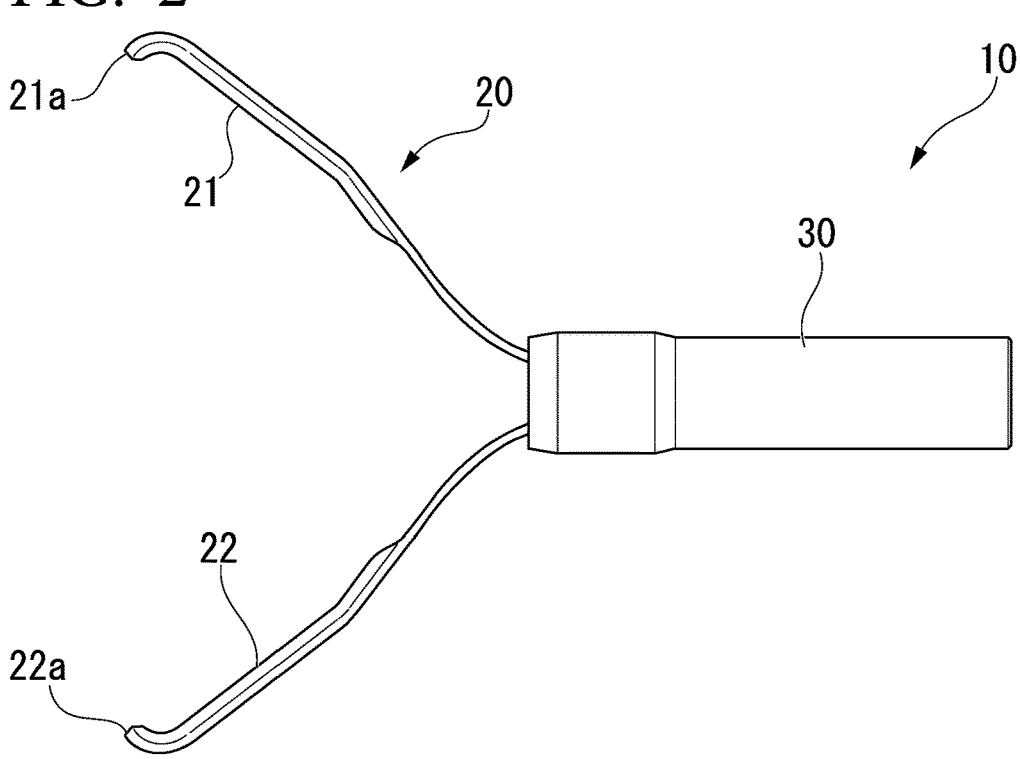
FIG. 2 is a view showing a clip unit of the ligation device.
Figure 3:
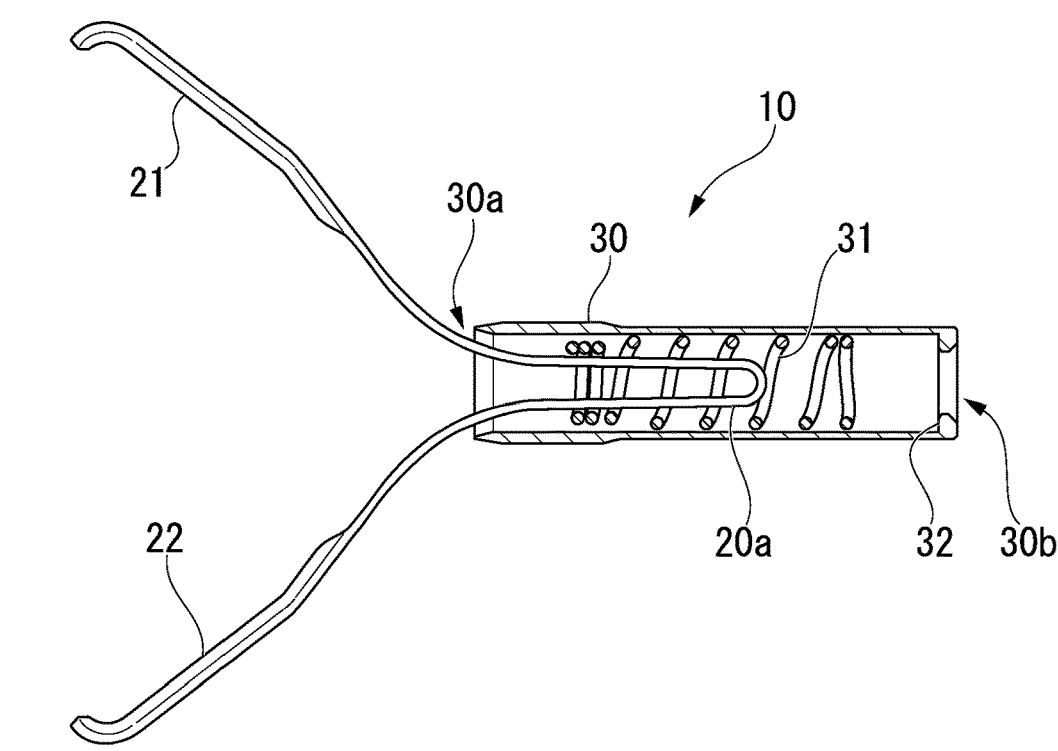
FIG. 3 is a cross-sectional view of the clip unit.

FIG. 2 is a view showing an appearance of the clip unit 10. FIG. 3 is a cross-sectional view of the clip unit 10. As shown in FIG. 2, the clip unit 10 includes an arm portion (treatment portion) 20 and a pressing tube (tubular member) 30 in which a part of the arm portion 20 is accommodated.

The arm portion 20 includes a pair of arms as a first arm 21 and a second arm 22. The first arm 21 and the second arm 22 have claws 21*a*, 22*a* at distal-end portions thereof, respectively. As shown in FIG. 3, the first arm 21 and the second arm 22 are connected at the proximal-end portion 20*a* of the arm portion 20. The proximal-end portion 20*a* is formed in a U shape.

The arm portion 20 is made of an alloy or metal. The examples of the material of the arm portion 20 include the stainless steel, the cobalt-chromium alloy, the nickel-titanium alloy, and the like.

The first arm 21 and the second arm 22 are expanded in the initial state as shown in FIG. 1. When the first arm 21 and the second arm 22 approach each other from the initial state, a biasing force to return to the initial state is generated due to the elastic force of the material.

The pressing tube 30 is a tubular member formed of metal, resin, or the like. As shown in FIG. 3, the proximal-end portion 20*a* of the arm portion 20 is accommodated in the pressing tube 30. The distal-end portion of the arm portion 20 protrudes from the distal-end opening 30*a* of the pressing tube 30. The proximal-end opening 30*b* of the pressing tube 30 is smaller than the distal-end opening 30*a*.

Figure 4:
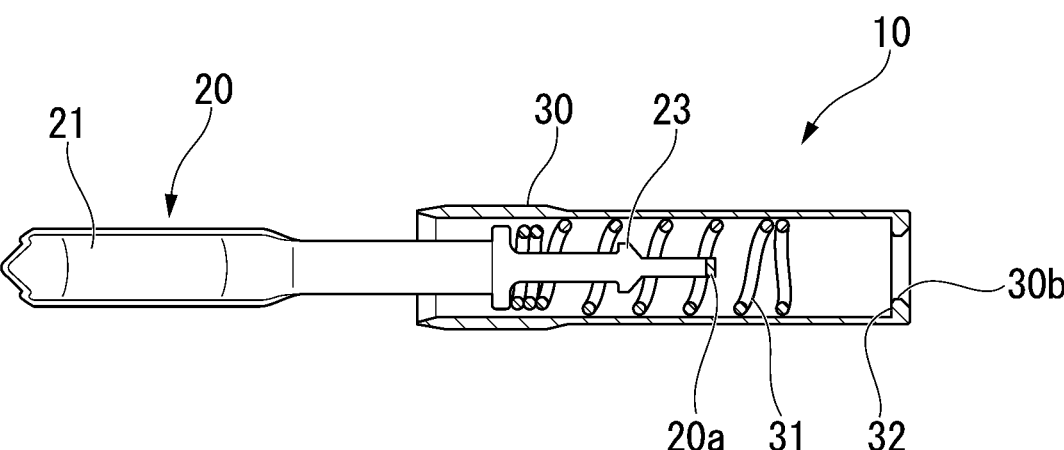
FIG. 4 is a cross-sectional view of the clip unit showing a cross section from a different direction from that in FIG. 3.

FIG. 4 is a view showing the inside of the pressing tube 30 as viewed from a direction different from that of FIG. 3. As shown in FIG. 4, a locking portion 23 is provided in an intermediate portion of each arm of the arm portion 20, and the dimensions in the width direction of each of arms 21, 22 at the locking portion 23 are increased (only the first arm 21 is visible in FIG. 4). Each locking portion 23 can pass through the proximal-end opening 30*b* when the first arm 21 and the second arm 22 approach each other. When the first arm 21 and the second arm 22 are separated from each other after passing through the proximal-end opening 30*b*, the locking portion 23 cannot pass through the proximal-end opening 30*b*. As a result, the arm portion 20 is locked with the pair of arms closed.

A coil spring 31 is arranged inside the pressing tube 30. The front end of the coil spring 31 can come into contact with the rear surfaces of the first arm 21 and the second arm 22. The rear end of the coil spring 31 can come into contact with the rear end surface 32 of the pressing tube 30 having the proximal-end opening 30*b*.

The basic structures of the arm portion 20 and the pressing tube 30 described above are known and are disclosed in PCT International Publication No. 2014/181676, for example.

As shown in FIG. 1, the actuator 50 includes an elongated insertion portion 51, an operation wire (power transmission member) 52 passed through the insertion portion 51, and an operation portion 60 connected to the insertion portion 51.

As the insertion portion 51, for example, a sheath formed of a coil can be used.

The operation portion 60 includes a main body 61 connected to the insertion unit 51 and a slider 62 slidably attached to the main body 61.

As the operation wire 52, for example, a stranded wire made of a metal wire can be used. The proximal-end portion of the operation wire 52 is connected to the slider 62. When the slider 62 is moved with respect to the main body 61, the operation wire 52 can be advanced and retracted in the insertion portion 51.

Figure 5:
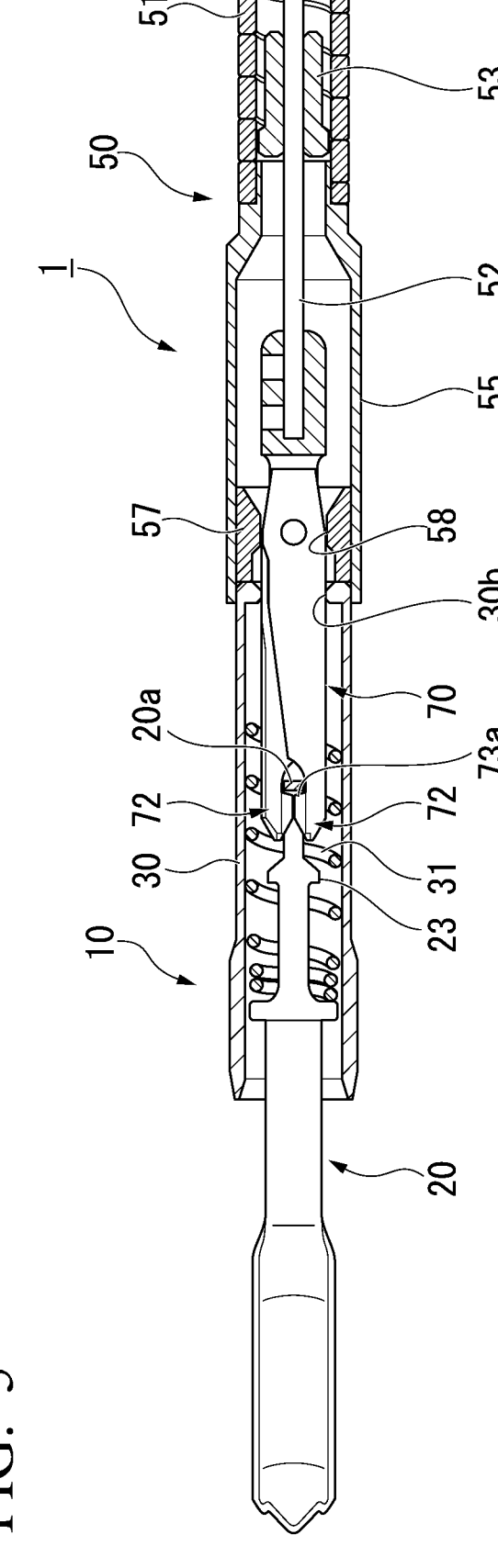
FIG. 5 is an enlarged cross-sectional view showing a clip mounting portion in the ligation device.

FIG. 5 is an enlarged cross-sectional view showing the distal-end portion of the actuator 50 to which the clip unit 10 is attached. A hook (connector) 70 that engages with the clip unit 10 is fixed to the distal end of the operation wire 52.

Figure 6:
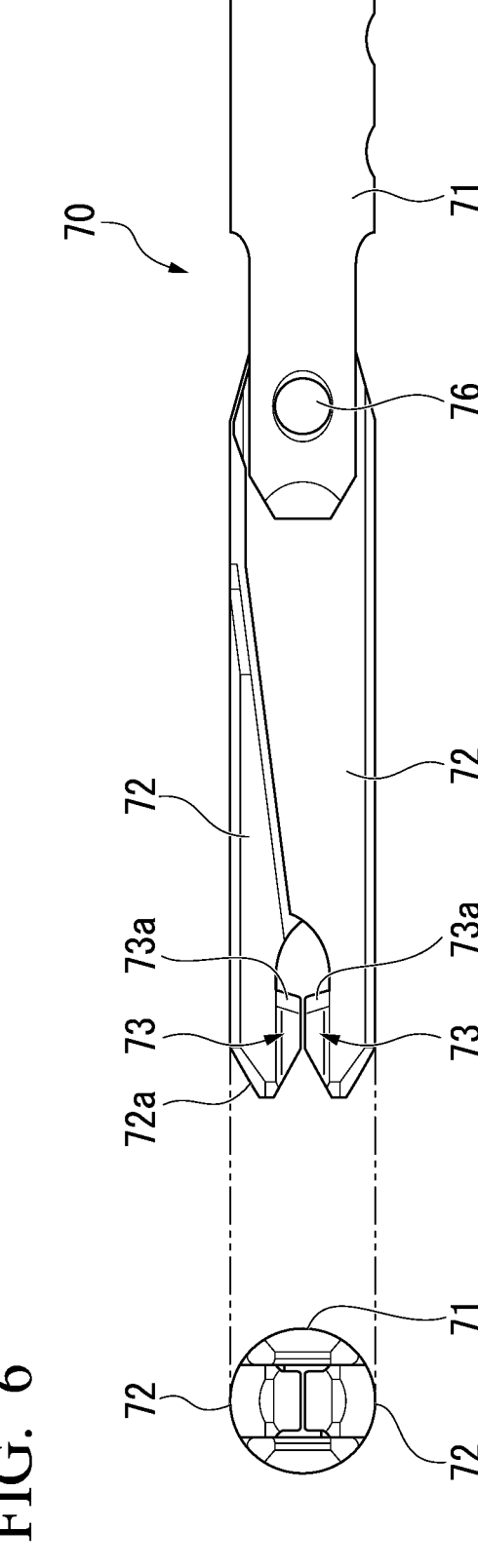
FIG. 6 is an enlarged view showing a hook.

FIG. 6 shows an enlarged view of the hook 70. The hook 70 includes a connection member 71 connected to the operation wire 52 and a pair of jaws 72 attached to the connection member 71.

The connection member 71 is fixed to the distal end of the operation wire 52 by brazing or the like. The pair of jaws 72 are members having the same shape and same size, and are pivotally supported by the connection member 71 in a state in which the claw portions 73 provided at the distal-end portions thereof face each other. That is, the pair of jaws 72 are configured to be able to approach and separate from each other by rotating around the shaft member 76 passed through the connection member 71.

Each jaw 72 includes a locking surface 73*a* at the rear end of the claw portion 73. The locking surface 73*a* is a surface on which the proximal-end portion 20*a* of the arm portion 20 is locked, and is formed in a U shape that matches the proximal-end portion 20*a*. Each locking surface 73*a* is inclined toward the distal end of the jaw 72 in a side view of the hook 70 as shown on the right side of FIG. 6.

The shape of the locking surface 73*a* is not limited to the U shape, and may be trapezoidal or rectangular.

The distal-end portion 72*a* of each jaw 72 gradually becomes smaller in the open-close direction (the direction in which the jaws 72 approach and separate from each other) as approaching the distal end. As shown in the front view of the hook 70 on the left side of FIG. 6, the dimensions of the hook 70 in the open-close direction are substantially the same except for the distal-end portion 72*a*.

As shown in FIG. 5, the operation wire 52 and the clip unit 10 are connected by the jaw 72 of the hook 70 clamping the proximal-end portion 20*a* of the arm portion 20. In a state in which the operation wire 52 and the clip unit 10 are connected, most of the hook 70 is located in the pressing tube 30, and the proximal-end portion 20*a* is engaged with the locking surface 73*a*. The external dimension of the hook 70 is slightly smaller than the inner diameter of the coil spring 31, and the hook 70 is movable inside the coil spring 31 without interfering with the coil spring 31.

As shown in FIG. 5, a rigid guide pipe 55 is attached to the distal end of the insertion portion 51. The inner diameter of a region on the distal-end side of the guide pipe 55 is larger than the outer diameter of the pressing tube 30, and the pressing tube 30 can enter therein. The rear end portion of the guide pipe 55 enters the insertion portion 51 and is fixed to the insertion portion 51 by welding or the like.

In the guide pipe 55, a regulation member 57 for preventing an unintentional disconnection between the proximal-end portion 20*a* and the hook 70 is arranged. The inner diameter of the regulation member 57 is the smallest in the small-diameter portion (connection-release prevention portion) 58. The inner diameter of the small-diameter portion 58 is smaller than the inner diameter of the proximal-end opening 30*b* of the pressing tube 30, and is slightly larger than the maximum dimension of the pair of jaws 72 in the open-close direction.

A stopper 53 is attached to the operation wire 52. Since the shape and dimensions of the stopper 53 are set such that the stopper cannot enter the guide pipe 55, when the stopper 53 comes into contact with the rear end of the guide pipe 55, the operation wire 52 cannot advance any further.

The operations of the ligation device 1 configured as described above when used will be described. The ligation device 1 is introduced into the body via the endoscopic channel. When inserting the ligation device 1 into the endoscope, the user retracts the slider 62 by a predetermined amount and inserts the ligation device 1 with the arm portion 20 in a closed and unlocked state. The clip unit 10 in which the arm portion 20 is closed and the distal-end portion of the insertion portion 51 may be inserted into the endoscope in a state of being housed in a separately prepared outer sheath.

When the ligation device 1 is protruded from the channel opening at the distal-end portion of the endoscope to reduce the pulling force of the slider or retract the outer sheath, the arm portion 20 advances with respect to the pressing tube 30 due to its own elastic restoration force and the elastic restoration of the coil spring 31. As a result, the pair of arms 21, 22 enter an open configuration. When the stopper comes into contact with the rear end of the guide pipe 55, the arm portion 20 cannot advance with respect to the pressing tube 30 such that the arm portion 20 does not fall off from the pressing tube 30 and maintains the open configuration.

When the user retracts the slider 62 with respect to the main body 61, the operation wire 52 and the hook 70 are pulled and the arm portion 20 retracts with respect to the pressing tube 30. As a result, the pair of arms 21, 22 are closed to enter a closed configuration. The user can ligate the tissue by locating the tissue between the pair of arms 21, 22 and closing the pair of arms 21, 22. By advancing the slider 62 with respect to the main body 61 until the locking operation described later is performed, the pair of arms 21, 22 can be transitioned from the closed configuration to the open configuration again. Therefore, in the ligation device 1, the clip unit 10 can be operated by the operation wire 52 to re-grasp the tissue until the locking operation is performed.

In a movement range of the operation wire 52 that the re-grasping can be performed, since the portion on the proximal-end side of the distal-end portion 72a of the pair of jaws 72 is located in the small-diameter portion 58, the engagement between the hook 70 and the proximal-end portion 20a is not released during the re-grasping operation.

When it is determined that the tissue located between the pair of arms 21, 22 may be ligated, the user performs the locking operation for fixing the arm portion 20 in the closed configuration. In the locking operation, the user further retracts the slider 62 with respect to the main body 61 beyond the range in which the re-grasping can be performed. When the slider 62 retracts, the operation wire 52 is pulled, and the pair of arms 21, 22 enter the pressing tube 30 in substantially parallel with each other while clamping the tissue. Furthermore, the locking portions 23 provided on the pair of arms 21, 22 approach each other to realize a positional relationship in which they can pass through the proximal-end opening 30b of the pressing tube 30.

The pair of locking portions 23 that have passed through the proximal-end opening 30b and moved out of the pressing tube 30 are separated again and are in a positional relationship in which they cannot pass through the proximal-end opening 30b. As a result, the pair of locking portions 23 come into contact with the proximal-end surface of the pressing tube 30 to prevent the arm portion 20 from protruding from the pressing tube 30, and the arm portion 20 is locked to maintain the closed configuration.

In the process of locking operation, the proximal-end portion 20a and the hook 70 move out of the pressing tube 30 through the proximal-end opening 30b. The operations of the hook 70 at this time will be described in detail below.

When the pair of jaws 72 clamping the proximal-end portion 20a is pulled, the proximal-end portion 20a tends to move toward the distal-end side of the jaw 72 along the inclined locking surface 73a. As a result, a force to open and separate the pair of jaws 72 from each other is applied on the pair of jaws 72. However, in the pressing tube 30, the pair of jaws 72 cannot be separated so much that the engagement between the proximal-end portion 20a and the hook 70 can be canceled such that the engagement between the proximal-end portion 20a and the hook 70 is not released in the pressing tube 30.

Figure 7:
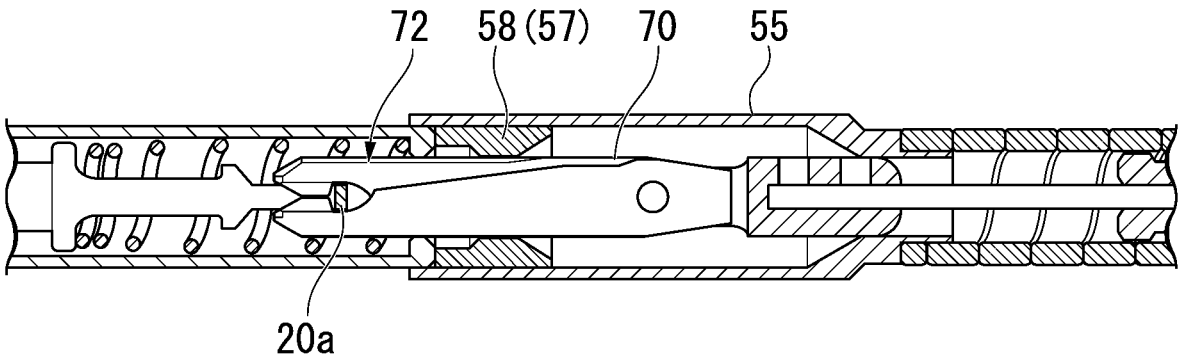
FIG. 7 is a partial cross-sectional view showing a processing during the usage of the ligation device.

The pulled jaws 72 gradually retract and enter the internal space of the guide pipe 55 as shown in FIG. 7. In the internal space of the guide pipe 55, the claw portions 73 of the pair of jaws 72 can be separated to the extent such that the engagement between the proximal-end portion 20a and the hook 70 can be canceled; however, the regulation member 57 is arranged on the distal-end side of the guide pipe 55 such that in a state in which the portion other than the distal-end portion of the jaws 72 is located in the small-diameter portion 58, the pair of jaws 72 are not sufficiently separated from each other, and the state in which the proximal-end portion 20a and the hook 70 are engaged with each other is maintained.

Figure 8:
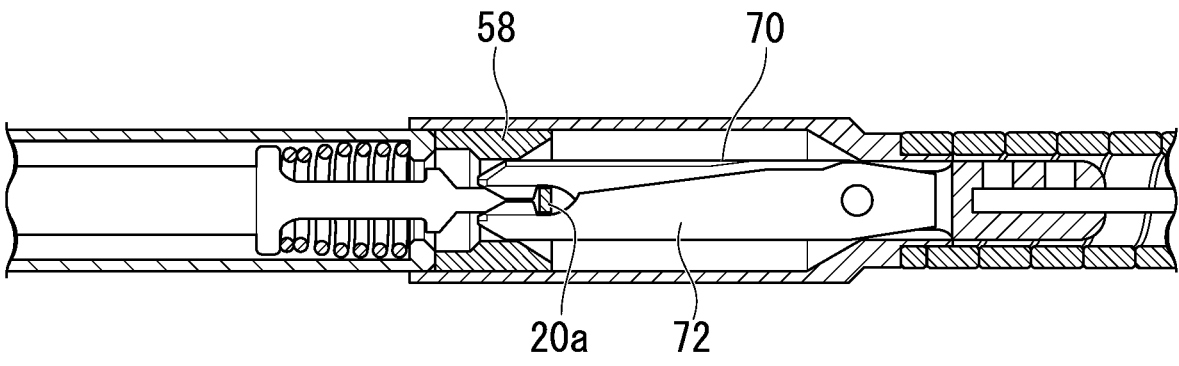
FIG. 8 is a partial cross-sectional view showing a processing during the usage of the ligation device.

When the jaws 72 are further retracted, the hook 70 comes out of the pressing tube 30, and the entire hook 70 moves into the internal space of the guide pipe 55 as shown in FIG. 8. Correspondingly, the proximal-end portion 20a also passes through the proximal-end opening 30b of the pressing tube 30 and moves out of the pressing tube 30; however, in the state shown in FIG. 8, the pair of jaws 72 are still sufficiently close to each other due to the small-diameter portion 58 such that the engagement between the proximal-end portion 20a and the hook 70 is not released.

In other words, the regulation member 57 prevents the claw portions 73 of the jaws 72 from being displaced in the direction separating from the longitudinal axis of the pressing tube 30 and falling off from the proximal end portion 20a.

When the user further retracts the slider 62, the arm portion 20 further retracts, and the locking portion 23 moves out of the pressing tube 30 through the proximal-end opening 30b. At this time, the portion of the jaws 72 other than the distal-end portion passes through the small-diameter portion 58, and the distal-end portion 72a of the jaws 72 reaches the small-diameter portion 58.

Figure 9:
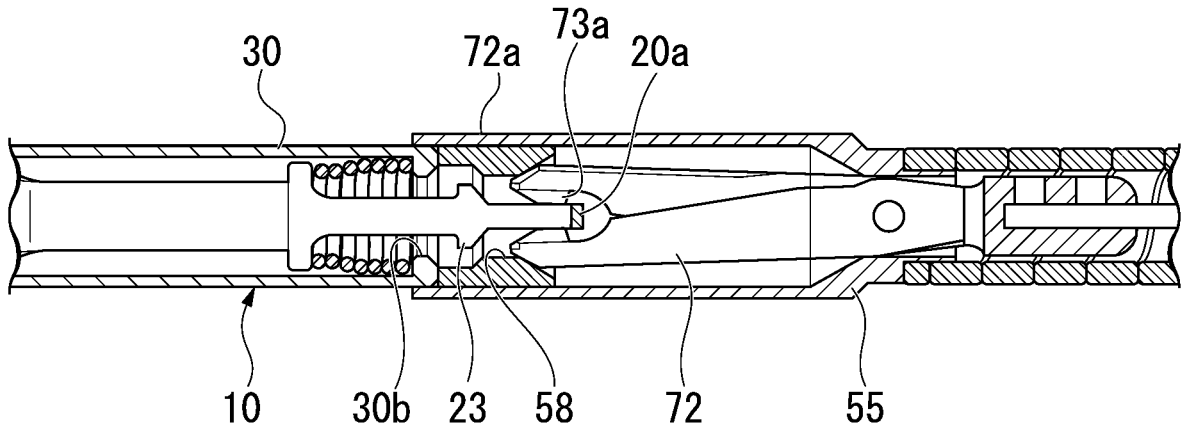
FIG. 9 is a partial cross-sectional view showing a processing during the usage of the ligation device.

Since the distal-end portion 72a of the pair of jaws 72 have smaller dimensions in the open-close direction, when the distal-end portion 72a is located at the small-diameter portion 58, a space for the pair of jaws 72 to separate from each other is generated in the small-diameter portion 58. As a result, due to the force received by the locking surface 73a from the proximal-end portion 20a of the arm portion 20, as shown in FIG. 9, the claw portions 73 of the pair of jaws 72 are separated from the proximal-end portion 20a in the guide pipe 55, and the engagement between the proximal-end portion 20a and the hook 70 is released. Furthermore, the locking portion 23 is engaged to the proximal-end surface of the pressing tube 30 such that the arm portion 20 is locked to be not to open, the pressing tube 30 is disengaged from the guide pipe 55 and the clip unit 10 is indwelled in the tissue.

When the user removes the endoscope and the actuator 50 outside the body, a series of procedures is completed.

As described above, according to the ligation device 1 according to the present embodiment, the dimensions and positional relationship between the small-diameter portion 58 and the jaws 72 in the actuator 50, and the locking portion 23 of the arm portion 20 and the proximal-end portion 20a in the clip unit 10, it is possible to realize the configuration that the engagement between the proximal-end portion 20a and the hook 70 will never be released until the arm is locked.

According to the ligation device 1, it is possible to re-grasp the tissue by the clip unit 10 while releasing the connection between the actuator 50 and the clip unit 10 by only pulling the operation wire 52 such that the operations become easy.

Since the inner diameter of the small-diameter portion 58 is smaller than the inner diameter of the proximal-end opening 30b, the contact and friction with the hook 70 occur exclusively in the small-diameter portion 58 in the guide pipe 55 rather than in the pressing tube. If the friction or catching occurs between the pressing tube 30 and the hook 70, it causes an event of a stack in which the arm portion cannot be opened again even though the locking portion 23 is inside the pressing tube 30. According to the structure of the ligation device 1, even if the operation wire is advanced in an attempt to open the arm when the stack has occurred, the entire clip unit advances with respect to the guide pipe together with the operation wire such that the stack is difficult to be resolved.

In the ligation device 1 according to the present embodiment, as described above, the engagement between the proximal-end portion 20a and the hook 70 will never be released until the arm is locked, such that the stacking is unlikely to occur.

If the contact or friction with the hook 70 occurs with the guide pipe 55, the advancement operation of the operation wire acts as a force for advancing the hook 70 with respect to the guide pipe 55 such that it is easy to resolve the stack when the stack should occur.

Even if the inner diameter of the small-diameter portion 58 and the inner diameter of the proximal-end opening 30b are the same, the contact and friction can be generated exclusively in the small-diameter portion 58 by tapering the shape of the hook 70 or the like, and the same effect is obtained. That is, in a state in which the small-diameter portion 58 is in contact with the hook 70, only the outer diameter of the portion of the hook 70 located at the proximal-end opening has to be smaller than the inner diameter of the proximal end opening.

The hook 70 may be slightly opened when it comes into contact with the small-diameter portion 58. In this case, if the distal-end portion of the hook 70 is not displaced outside the diameter range of the proximal-end opening, the arm portion can be prevented from being stuck.

Figure 10:
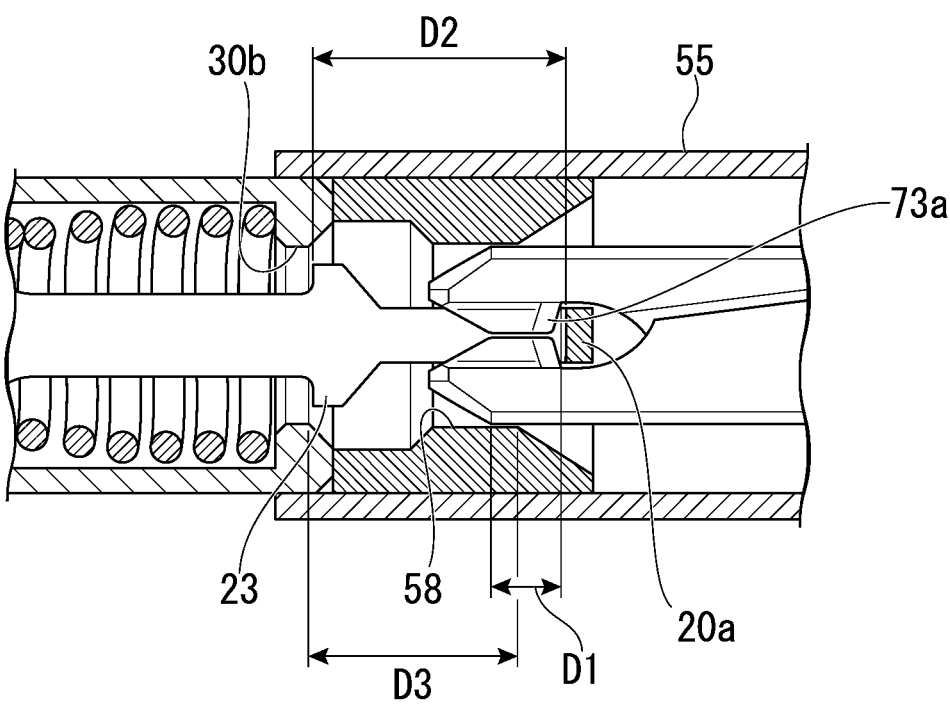
FIG. 10 is an enlarged view showing a connection portion of an operation wire and an arm portion in the ligation device.

In order to realize the above-mentioned operations of the hook, a relationship among a distance D1 in the axial direction of the tubular shape of the guide pipe 55 between the rear end of the distal-end portion 72a and the locking surface 73a where the size of the jaws 72 begins to decrease, a distance D2 in the axial direction of the tubular shape of the pressing tube 30 between the front end of the portion 23 and the front end of the proximal-end portion 20a, and a distance D3 in the axial direction of the guide pipe 55 between the rear end of the small-diameter portion that causes the locking function at the proximal-end opening 30b and the rear end 58b of the small diameter portion 58 is important. The distances D1 to D3 are shown in FIG. 10.

$$D2-D1<D3 \tag{1}$$

8

That is, by setting the dimensions of each portion to satisfy the relationship described by above equation (1), it is possible to secure that the part other than the distal-end portion 72a of the jaws 72 is positioned at the small-diameter portion 58 until the locking portion 23 moves out of the pressing tube 30.

Also, in the jaws 72, when the distance from the shaft member 76 to the distal-end portion 72a is increased, the opening angle when the pair of jaws are separated from each other becomes smaller. As a result, when the jaws 72 advance to re-grasp the arm portion, it is less likely to interfere with the proximal-end opening 30b of the pressing tube 30.

Figure 11:
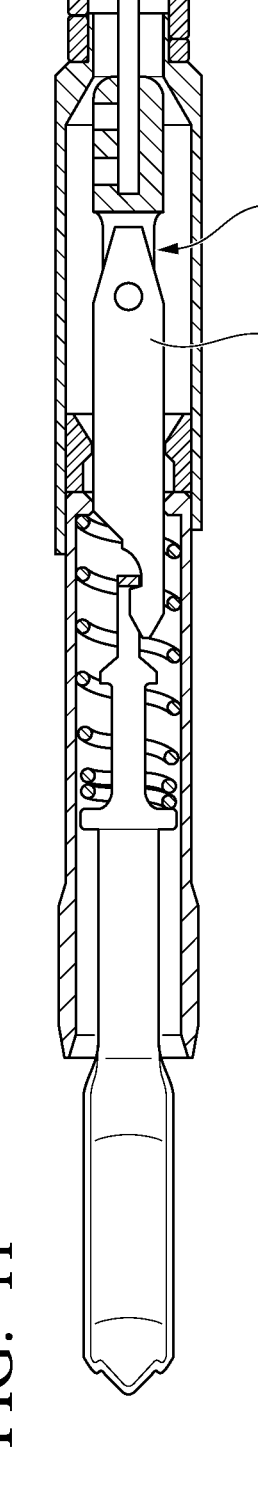
FIG. 11 is an enlarged cross-sectional view showing the clip mounting portion according to a modification example of the ligation device.
Figure 12:
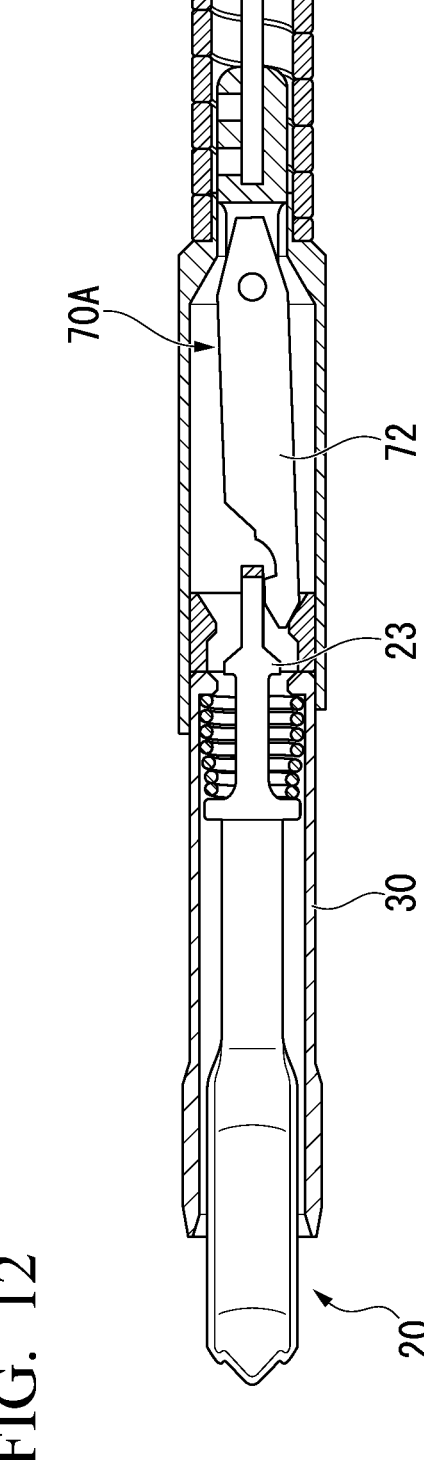
FIG. 12 is a partial cross-sectional view in a processing during the usage of the ligation device according to the modification example.

According to the present embodiment, the hook 70 is not limited to the double-swing door configuration including a pair of jaws. The hook 70A as shown in FIG. 11 includes only one jaw 72. Even in such a hook 70A, by making the same settings as described above, as shown in FIG. 12, it is possible to configure that the engagement between the hook 70A and the arm portion 20 is not released until the locking portion 23 has moved out of the pressing tube 30.

In a case that the configuration is provided with only one jaw, the balance may be adjusted so as to smoothly release the connection between the arm portion and the jaw by offsetting the proximal-end portion of the arm portion and the locking surface of the jaw from the central axis of the pressing tube or the guide pipe, if necessary.

According to the present embodiment, the pressing tube 30 may be configured to not to enter the guide pipe 55 but may simply come into contact with the guide pipe 55.

Also, the stopper 53 may be provided at a position different from the above-mentioned position. For example, the position where the slider 62 interferes with the main body 61 and cannot advance may function as the stopper. Furthermore, the stopper 53 may not be provided.

Another exemplary embodiment of the present disclosure will be described with reference to FIG. 13 to FIG. 16. In the following description, the same reference signs will be designated to the configurations common to those already described, and duplicate description will be omitted.

Figure 13:
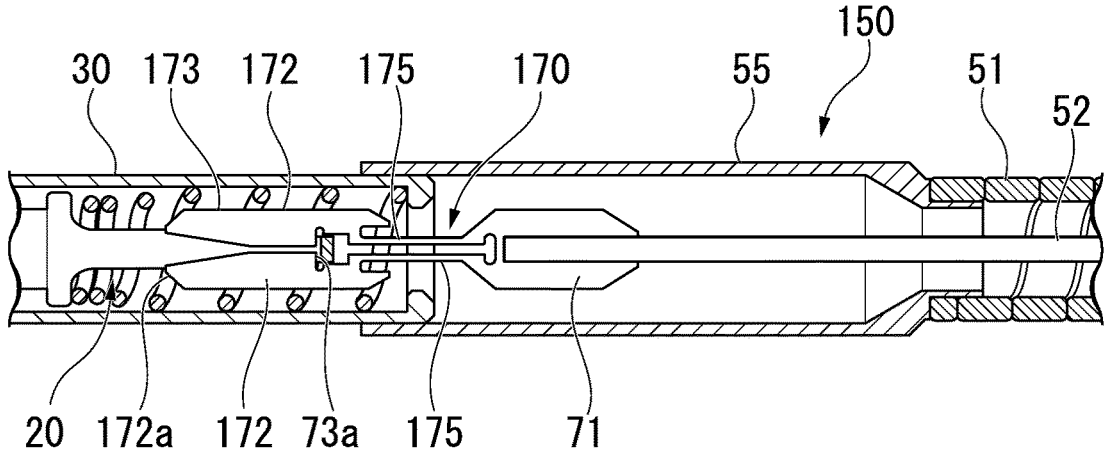
FIG. 13 is an enlarged cross-sectional view showing the clip mounting portion in a ligation device according to an exemplary embodiment of the present disclosure.

FIG. 13 is a cross-sectional view showing the periphery of the guide pipe 55 of the actuator 150 according to the present embodiment. The regulation member 57 is not arranged on the guide pipe 55.

The operation wire 52 and the arm portion 20 are connected by a hook 170. The hook 170 includes a connection member 71 and a pair of jaws 172. Each jaw 172 and the connection member 71 are connected by a leaf spring-shaped link 175, and the pair of jaws 172 can be separated from each other by deforming the link 175.

Each jaw 172 has a claw portion 173 and a locking surface 173a. Different from the above embodiment, the locking surface 173a is orthogonal to or substantially orthogonal to the longitudinal direction of the guide pipe. Similar to the above embodiment, the distal-end portion 172a gradually decreases in size in the open-close direction as approaching toward the distal end.

According to the present embodiment, the relationship between the above-mentioned distance D1 and the distance D2 as shown in FIG. 13 satisfies the following equation 2. Since the regulation member 57 does not exist, the distance D3 does not exist in the present embodiment.

$$D1>D2 \tag{2}$$

Figure 14:
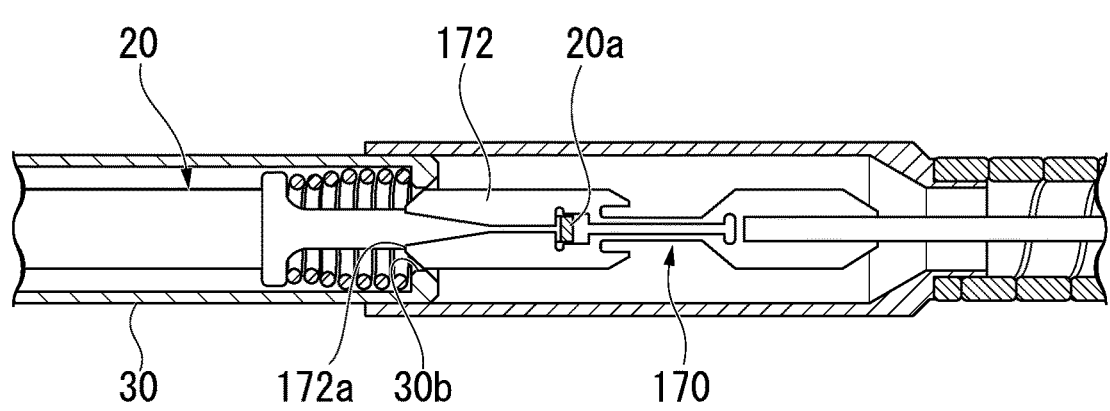
FIG. 14 is a partial cross-sectional view showing a processing during the usage of the ligation device.

In the ligation device according to the present embodiment provided with the actuator 150, the hook 170 and the arm portion 20 satisfy the above equation such that, as shown in FIG. 14, even after the proximal-end portion 20*a* moves out of the pressing tube 30, while the locking portion 23 is located in the pressing tube 30, the portion other than the distal-end portion 172*a* of the jaw 172 is always located in the proximal end opening 30*b*. As a result, it is possible to prevent the opening of the jaw 172 to cancel the connection between the hook 170 and the arm portion 20 by the edge of the proximal-end opening 30*b*.

Figure 15:
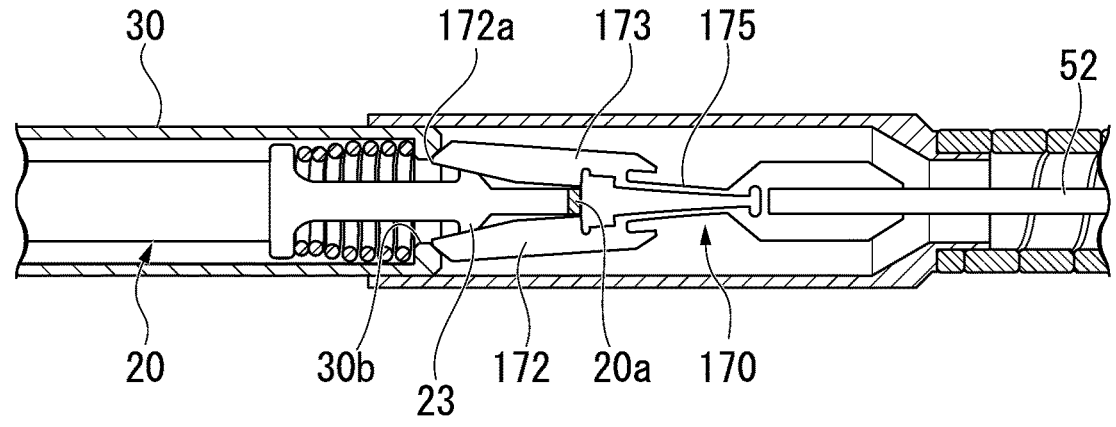
FIG. 15 is a partial cross-sectional view showing a processing during the usage of the ligation device.

When the distal-end portion 172*a* of each jaw 172 reaches the proximal-end opening 30*b*, each claw portion 173 rotates due to the force received from the proximal-end portion 20*a*, and the distal-end portions 172*a* are separated from each other. After that, each link 175 is deformed and the pair of jaws 172 are further separated from each other, and as shown in FIG. 15, the engagement between the hook 170 and the arm portion 20 is released. At this time, the locking portion 23 has completely moved out of the pressing tube 30, and the arm portion 20 separated from the hook 170 is locked.

Also according to the present embodiment, similar to the above embodiment, it is possible to release the connection between the actuator and the clip unit by only pulling the operation wire 52 to make the operations easy. Furthermore, the stacking is unlikely to occur.

Further, since the circumferential edge portion of the proximal-end opening 30*b* functions as a disconnection prevention portion, the regulation member 57 is not required and the manufacturing is simple.

According to the present embodiment, if the above equation (2) is satisfied, the structure of the hook 70 to which a pair of jaws are rotatably attached can also be adopted.

On the contrary, if the equation (1) is satisfied, the structure of the hook 170 can be applied to the configuration according to the above embodiment.

Figure 16:
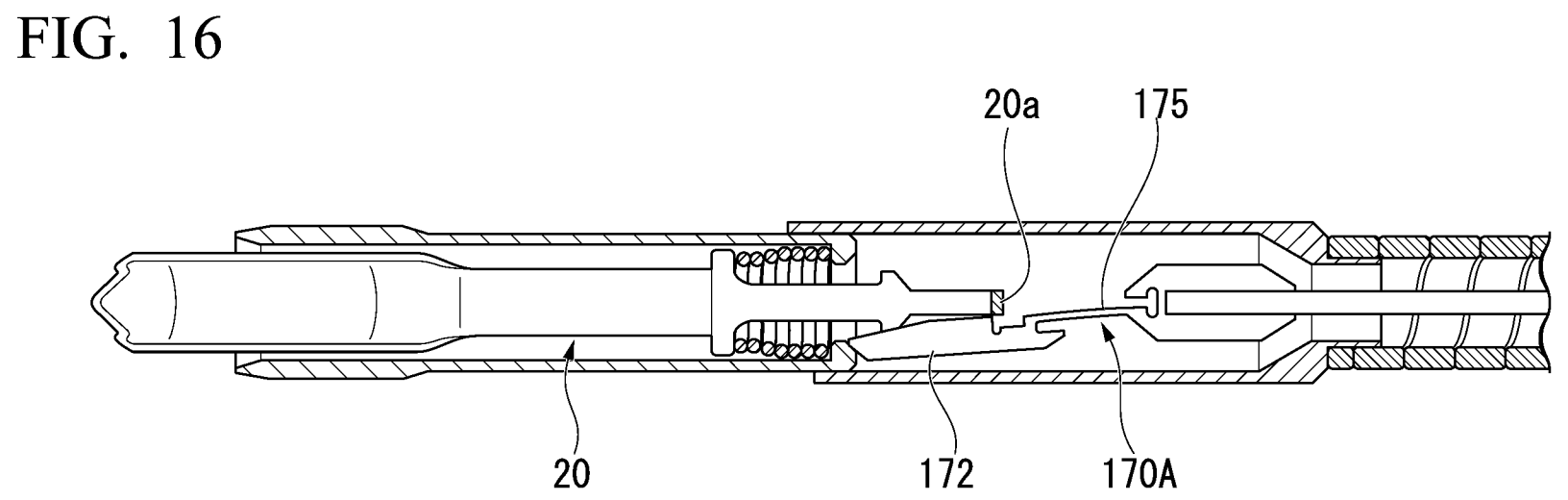

According to the present embodiment, the hook 170 does not have to include a pair of jaws. The hook 170A as shown in FIG. 16 has only one jaw 172; however, by satisfying the above equation (2), as shown in FIG. 16, the connection with the arm portion 20 is released in substantially the same manner as the hook 170.

According to the present embodiment, the connection between the hook 170 and the arm portion 20 may be released by breaking the link 175. In the present embodiment, the circumferential edge portion of the proximal-end opening 30*b* suppresses the link 175 from being displaced in the direction separating from the longitudinal axis of the pressing tube 30, and appropriately apply a force on the link 175 to break the link 175 at an appropriate timing. This aspect can be applied to both the case of configuring a pair of jaws and the case of configuring only one jaw.

The broken portion is not limited to the connector, and may be the power transmission member.

Although each embodiment of the present disclosure has been described above, the technical scope of the present disclosure is not limited to the above-described embodiment, and various changes and deletions may be made to each component within a range that does not deviate from the scope of the present disclosure.

The indwelling device according to the present disclosure is not limited to the clip unit described above. For example, it may be a snare wire that can be indwelled in the body in a ligated state as described in Japanese Patent No. 4981157.

The power transmission member according to the present disclosure is not limited to the above-mentioned wire. For example, when the present disclosure is applied to a treatment tool or the like used under a laparoscope, the power transmission member may be a rigid rod.

The claw portion according to the present disclosure does not have to include a distal-end portion whose dimensions in the open-close direction gradually decrease. When the dimensions of the claw portion in the open-close direction are the same up to the distal end thereof, the setting based on the above equation (1) and equation (2) may be performed with the distal end of the claw portion as a reference.

In the present disclosure, it is not essential to arrange the coil spring in the pressing tube. That is, the advancement of the arm portion may not be assisted by the coil spring; however, the advancement of the arm portion may be performed only by the advancement of the operation wire.

The arm portion and the pressing tube may be locked at a portion other than the proximal-end opening. Also in this case, by designing the connector to be located in the pressing tube until it is locked, it is possible to prevent the arm portion from being stuck.

Although the preferred embodiments of the present disclosure have been described above, the present disclosure is not limited to these embodiments. Configurations can be added, omitted, replaced, and other modifications without departing from the scope of the present disclosure. Further, the present disclosure is not limited by the above description, but is limited only by the appended claims.

What is claimed is:

1. A clip device, comprising:
a holder extending along a longitudinal axis and including an engaged portion;
arms that are configured to be at least partially accommodated in the holder and including an engaging portion configured to fix the arms to the holder by engaging with the engaged portion;
a connector releasably connected to the arms;
a pipe including a space configured to accommodate the connector when the engaging portion is engaged with the engaged portion, the connector being configured to separate from the arms within the space; and
a regulation portion formed as a small-diameter portion in the pipe and configured to regulate a displacement of the connector in a direction separating from the longitudinal axis in a state in which the engaging portion is arranged at a distal end side of the engaged portion.

2. The clip device according to claim 1, wherein
the engaging portion is a protrusion extending in the direction separating from the longitudinal axis of the holder, and
the arms are configured to be pulled in a proximal direction along the longitudinal axis of the holder such that the engaging portion is arranged at a proximal-end side of the engaged portion so as to be engageable with the engaged portion.

3. The clip device according to claim 1, wherein
the regulation portion is the small-diameter portion provided at a proximal-end side of the engaged portion of the holder and through which the connector is able to pass, and
a diameter of the small-diameter portion is equal to or less than a diameter of the engaged portion.

4. The clip device according to claim 3, wherein
the connector includes a claw that is configured to engage with the arms,
the connector is configured to be disconnected from the arms by separating the claw from the arms, and
the claw is arranged inwardly in a diameter direction of the small-diameter portion in a state in which the engaging portion is engaged with the engaged portion.

5. The clip device according to claim 1, wherein
the connector includes an engaging surface configured to engage the arms, and
a distance between the engaging surface and a distal-end portion of the connector is larger than a distance between the engaging surface and the engaged portion in the state in which the arms are fixed to the holder.

6. The clip device according to claim 1, wherein
the connector includes an engaging surface configured to engage the arms, and
a distance between the engaging surface and a distal-end portion of the connector is larger than a distance between the engaging portion and a proximal-end portion of the arms.

7. The clip device according to claim 1, wherein the regulation portion is provided in the pipe.

8. The clip device according to claim 7, wherein:
the pipe is connected to a distal end of a sheath;
the sheath is configured to be inserted with a wire; and
the wire is connected to the connector.

9. The clip device according to claim 1, wherein the regulation portion configured to regulate the displacement of the connector in the direction separating from the longitudinal axis in a state in which the engaging portion is arranged at a distal-end side of the engaged portion and the connector is accommodated in the pipe.

10. The clip device according to claim 1, wherein the regulation portion configured to regulate the displacement of the connector in the direction separating from the longitudinal axis in a state in which the engaging portion is arranged at a distal-end side of the engaged portion, the connector is accommodated in the pipe, and the holder contacts the pipe.

11. The clip device according to claim 1, wherein the holder is a tube and includes a proximal-end opening and the engaged portion is the proximal-end opening.

12. The clip device according to claim 11, wherein the connector is arranged at a distal-end side of the proximal-end opening in a state in which the arms protrude from a distal end of the holder.

13. The clip device according to claim 1, wherein the connector includes an engaging surface configured to engage the arms, and
a distance between the engaging surface and a distal-end portion of the connector is smaller than a distance between the engaging portion and a proximal-end portion of the arms.

14. The clip device according to claim 1, wherein the connector is allowed to displace in the direction separating from the longitudinal axis in a state in which the connector is arranged at a distal or proximal end side of the regulation portion.

15. The clip device according to claim 14, wherein the connector is configured to be displaced in the direction separating from the longitudinal axis upon receiving a force from the arms.

16. The clip device according to claim 1, wherein the connector is configured to be regulated from displacement by the regulation portion until the engaging portion is arranged at a proximal-end side of the engaged portion.

17. A clip device, comprising:
a holder extending along a longitudinal axis and including an engaged portion;
an arm member configured to be at least partially accommodated in the holder and including an engaging portion configured to fix the arm member to the holder by engaging with the engaged portion;
a connector releasably connected to the arm member;
a pipe including a space configured to accommodate the connector when the engaging portion is engaged with the engaged portion, wherein the connector is configured to be separated from the arm member within the space; and
a regulation portion formed as a small-diameter portion in the pipe and configured to regulate a displacement of the connector in a direction separating from the longitudinal axis in a state in which the engaging portion is arranged at a distal end side of the engaged portion and the connector is accommodated in the pipe.

18. The clip device according to claim 17, wherein
the regulation portion is provided in the pipe, the pipe is connected to a distal end of a sheath;
the sheath is configured to be inserted with a wire; and
the wire is connected to the connector.

19. The clip device according to claim 17, wherein
the connector includes an engaging surface configured to engage the arm member, and
a distance between the engaging surface and a distal-end portion of the connector is smaller than a distance between the engaging portion and a proximal-end portion of the arm member.

20. The clip device according to claim 17, wherein
the connector is allowed to displace in the direction separating from the longitudinal axis in a state in which the connector is arranged at a distal or proximal end side of the regulation portion and
the connector is configured to be displaced in the direction separating from the longitudinal axis upon receiving a force from the arm member.

* * * * *